(12) United States Patent
Foumenteze et al.

(10) Patent No.: US 11,389,158 B2
(45) Date of Patent: Jul. 19, 2022

(54) SURGICAL THREAD

(71) Applicant: THREAD & LIFT, Brussels (BE)

(72) Inventors: Jean-Paul Foumenteze, Vallauris (FR); Vincent Foumenteze, Saint-Gilles (BE)

(73) Assignee: THREAD & LIFT, Brussels (BE)

( * ) Notice: Subject to any disclaimer, the term of this patent is extended or adjusted under 35 U.S.C. 154(b) by 93 days.

(21) Appl. No.: 16/652,523

(22) PCT Filed: Oct. 8, 2018

(86) PCT No.: PCT/EP2018/077311
§ 371 (c)(1),
(2) Date: Mar. 31, 2020

(87) PCT Pub. No.: WO2019/068928
PCT Pub. Date: Apr. 11, 2019

(65) Prior Publication Data
US 2020/0281588 A1    Sep. 10, 2020

(30) Foreign Application Priority Data
Oct. 6, 2017  (EP) ..................................... 17195269

(51) Int. Cl.
*A61B 17/06* (2006.01)
(52) U.S. Cl.
CPC .................. *A61B 17/06166* (2013.01); *A61B 2017/06176* (2013.01); *A61B 2017/06185* (2013.01)
(58) Field of Classification Search
CPC .......... A61B 17/12009; A61B 17/0487; A61B 17/06166; A61B 2017/06185; A61B 2017/06176

USPC ........................................................ 606/228
See application file for complete search history.

(56) References Cited

U.S. PATENT DOCUMENTS

| | | | |
|---|---|---|---|
| 8,118,834 B1* | 2/2012 | Goraltchouk | .... A61B 17/06166 606/228 |
| 8,641,732 B1 | 2/2014 | Goraltchouk et al. | |
| 2003/0149447 A1 | 8/2003 | Morency et al. | |
| 2007/0293892 A1 | 12/2007 | Takasu | |
| 2015/0073474 A1* | 3/2015 | Hodgkinson | .... A61B 17/06166 606/228 |

FOREIGN PATENT DOCUMENTS

| | | |
|---|---|---|
| EP | 3202336 A1 | 8/2017 |
| WO | 2005096956 A1 | 10/2005 |
| WO | 2012116319 A2 | 8/2012 |
| WO | 2016135474 A1 | 9/2016 |

OTHER PUBLICATIONS

International Search Report (and English translation) and Written Opinion of the International Searching Authority for International Application No. PCT/EP2018/077311 dated Dec. 20, 2018.

* cited by examiner

*Primary Examiner* — Katherine H Schwiker
*Assistant Examiner* — Serenity A Miller
(74) *Attorney, Agent, or Firm* — Heslin Rothenberg Farley & Mesiti, P.C.

(57) ABSTRACT

The present invention relates to a surgical thread including at least a first portion extending longitudinally and comprising a central thread covered with a sheath. The sheath includes fastening means each including at least one conical barb. The present invention also relates to a medical device including such a surgical thread and a surgical needle.

13 Claims, 3 Drawing Sheets

SURGICAL THREAD

CROSS REFERENCE TO RELATED APPLICATIONS

This application is a national stage filing under 35 U.S.C. § 371 of International Application No. PCT/EP2018/077311, filed on Oct. 8, 2018, published as WO 2019068928 on Apr. 11, 2019, and claims priority to European Patent Application No. 17195269.0, filed Oct. 6, 2017. The entire disclosures of each of the said applications are incorporated by reference in their entireties herein.

FIELD OF THE INVENTION

The present invention relates to a surgical thread. In particular, the present invention relates to a surgical thread for medicine, cosmetic medicine and cosmetic surgery used particularly for corrective facial surgery also known as "facelift" surgery.

STATE OF THE RELATED ART

Over time, subcutaneous facial tissue, also known as hypodermis or subcutaneous fat, sags, pulling the facial skin down with it. This sagging is recognised as being essentially the result of gravity acting upon the face wherein the connective fibres slacken as well as of peripheral bone resorption. This ageing is referred to medically as facial "ptosis".

To prevent facial skin from sagging, several surgical techniques included under the generic name "lift" are known. This lift may be referred to as "malar", "cervicofacial", or otherwise depending on the area treated as well as the procedure involved. It generally consists of making an incision in the skin, lifting it, repositioning the subcutaneous and superficial muscle tissue and then excising the excess lifted skin. This technique makes it possible to treat the problem of "ptosis" but tends to leave scars along the various incisions as well as damage the subcutaneous tissue irremediably. Furthermore, this technique is frequently declined by the patient due to the irreversible and not always natural result.

A more recent practice consists of using surgical threads for repositioning sagging subcutaneous facial tissue. This technique does not involve major surgical procedures. These threads are implanted under the facial skin using foam-tipped needles leaving no visible mark.

The patent application US2007/0293892 is particularly known, describing a surgical thread for plastic surgery comprising a central part and two distal parts, the distal parts comprising projections to secure the thread in the subcutaneous and superficial muscle tissue. The projections from each distal part are oriented on the same side to allow the thread to pass through the skin in one direction and to impede the thread from shifting in the opposite direction by the fastening of the projections in the patient's subcutaneous and/or superficial muscle tissue. The projections are obtained by cutting, in the longitudinal direction of the thread, a thin part which, on straightening, will form a projection. This type of projection formed will obligatorily comprise a sharp distal end. This tip at the end of the projection has the drawback of being aggressive for the patient's subcutaneous and/or superficial muscle tissue and is therefore very painful on insertion and in the patient's day-to-day life.

The international application WO2005/096956 is also known, describing a similar thread wherein the projections are produced by cutting, in the body of the thread, parts that will straighten. These projections for securing the thread in the subcutaneous and superficial muscle tissue are arranged in a spiral around the thread.

Finally, the document WO2016/135474 is known, describing a resorbable suture thread comprising bioresorbable elements of elongate shape comprising a hole along the longitudinal axis thereof suitable for pushing the suture thread through.

However, the latter two solutions have the drawback of not adhering optimally to the subcutaneous and superficial muscle tissue.

The aim of the present invention is that of developing a surgical thread suitable for optimising the strength of the thread in the subcutaneous and/or superficial muscle tissue, and having adapted mechanical properties and a simple and reproducible manufacturing method.

SUMMARY

The present invention relates to a surgical thread comprising at least a first portion extending longitudinally and comprising a central thread covered with a sheath, said sheath comprising fastening means each comprising at least one conical barb.

In an embodiment, the fastening means are formed with the sheath, particularly without cutting, directly in the form of conical barbs each having an angle of inclination between 10° and 75° with the longitudinal axis of the surgical thread.

The structure of the surgical thread in two elements, namely, on one hand, a core formed by the central thread and, on the other, a sheath comprising fastening means in the form of conical barbs, makes it possible to give each element mechanical properties adapted to the function thereof. In particular, the core formed by the central thread, which provides the overall mechanical strength of the surgical thread, must have a satisfactory tensile strength and a satisfactory breaking strength while remaining flexible. Preferably, the central thread has little or no elasticity. The sheath, which bears the conical fastening barbs, must have a satisfactory rigidity to prevent the conical barbs from turning over under the pressure of the bonded fibres, while have a gentle and flexible interaction with the patient's soft tissue making it possible to prevent the inflammation and/or weakening thereof. The structure of the surgical thread in two elements makes it possible to obtain optimal mechanical properties of the surgical thread by designing the two elements independently from one another, which is not possible in the case of a one-piece surgical thread where a compromise is needed to reconcile the mechanical properties required for the main part of the thread and the fastening means.

According to an embodiment, the central thread and the sheath are based on the same material having different characteristics for either element, particularly due to a treatment, a state (particularly pasty) or a different use of the material for each element. By way of example, the central thread and the sheath may be based on the same linear polymer material, where the polymer material of the sheath has undergone a stretching process that the polymer material of the central thread has not undergone, such that the sheath has a higher modulus of elasticity along the stretching axis than that of the central thread.

According to a further embodiment, the central thread and the sheath are based on different materials, particularly based on different polymer materials, chosen to give specific mechanical properties to each element. In an embodiment, the central thread is made of polyester or of polyethylene terephthalate, and/or the sheath is made of silicone or of polyurethane elastomer.

In an embodiment, the central thread comprises a textile material including filament yarns, particularly felted, braided or woven filament yarns. In particular, the filament yarns may be based on polymer material, for example polyester or polyethylene terephthalate filament yarns. A textile structure of the central thread makes it possible to achieve satisfactory levels of breaking strength, while retaining the flexibility of the central thread. Indeed, the mechanical strength of the central thread may be increased by increasing the number of filament yarns, rather than through an increase in the diameter of the filament yarns which would result in excessive rigidity.

Thanks to the two-element structure of the surgical thread according to the invention, it is also possible to equip the central thread with sheaths at certain locations, and to leave same unsheathed at other locations, particularly at the level of portions intended to engage with a needle or marking portions for the surgeon, which do not need to be equipped with fastening means.

According to the invention, the fastening means are formed with the sheath, i.e. manufactured in one piece with the sheath, directly in the form of conical barbs each having an angle of inclination between 10° and 75° with the longitudinal axis of the surgical thread, so as to ensure fastening in the tissue. Advantageously, the sheath incorporating the conical barbs is manufactured in a single step, without requiring reworking to form the barbs, particularly without cutting or any other forming of the barbs in a further manufacturing step. The result is a simple manufacturing process for surgical thread. Furthermore, the shape of the barb formed may advantageously be defined to obtain optimised fastening in the tissue.

In an embodiment, the conical barbs are obtained by moulding the sheath, particularly by injection moulding. According to an embodiment, the surgical thread is obtained by over-moulding the sheath around the central thread, by placing the central thread in a mould and injecting the material from the sheath into the mould around the central thread.

The manufacture of the sheath by moulding makes it possible to obtain a reproducible barb shape from one barb to another and one surgical thread to another, which is not the case of cut barbs, particularly due to the movements of the thread during cutting and the lack of cutting precision for the barb sizes in question. Furthermore, manufacture by moulding makes it possible to obtain a conical shape easily, with a rounded distal end of the barbs, unlike cutting which tends to create a tip at the top of the barb and to generate a barb having non-uniform sides. A rounded distal end, particularly in a semi-circle, of the barbs may be formed in particular in the geometric extension of straight edges of the barb. Advantageously, a rounded distal barb end is less aggressive for the patient's tissue, without reducing the fastening capability of the barb which is provided primarily by the angular part at the base of the barb.

In an embodiment, the surgical thread further comprises:
 a second portion extending longitudinally and comprising
  a central thread covered with a sheath comprising fastening means each comprising at least one conical barb;
 a third portion devoid of fastening means and situated between the first portion and the second portion.

In an embodiment, the conical barbs are inclined and form an angle with respect to the longitudinal axis of the surgical thread preferentially of substantially 60°.

In an embodiment, said conical barbs comprise a spherical or rounded distal end.

In an embodiment, said fastening means comprise N conical barbs not spaced longitudinally and regularly spaced angularly by an angle $\theta_1$ and wherein N is an integer equal to or greater than 2.

In an embodiment, the fastening means comprise the same number N of barbs.

In an embodiment, the conical barbs of each fastening means are offset in rotation by an angle $\theta_3$ with respect to the conical barbs of the adjacent fastening means and wherein the angle $\theta_3$ is strictly greater than 0° and strictly less than the angle $\theta_1$.

In an embodiment, the fastening means each comprise four conical barbs.

In an embodiment, the angle $\theta_3$ is substantially equal to 45°.

In an embodiment, the conical barbs are inclined with respect to the longitudinal axis of the surgical thread in the direction of the third portion.

In an embodiment, the surgical thread further comprises an extension portion at each longitudinal end of the surgical thread.

The invention also relates to a medical device comprising a surgical thread according to the invention and at least one surgical needle connected to the surgical thread at one of the longitudinal ends thereof.

The invention also relates to a method for manufacturing a surgical thread comprising at least a first portion extending longitudinally and comprising a central thread covered with a sheath, said sheath comprising fastening means each comprising at least one conical barb, wherein the fastening means are formed during the manufacture of the sheath directly in the form of conical barbs each having an angle of inclination between 10° and 75° with the longitudinal axis of the surgical thread.

According to an embodiment, the sheath is obtained by moulding and the fastening means are formed during the moulding of the sheath.

In an embodiment, the sheath is obtained by injection moulding. In an embodiment, the surgical thread is obtained by placing the central thread in a mould and by injecting the material of the sheath around the central thread.

Definitions

In the present invention, the terms hereinafter are defined as follows:
 "Thread": relates to a flexible object extending longitudinally and wherein one of the three dimensions has a length at least 10 times greater than the two other dimensions. The cylindrical part extending longitudinally along this thread is referred to as the thread body.
 "Barb": relates to a projection from the thread body and capable of fastening the subcutaneous and superficial muscle tissue. A barb comprises a base at the level of the thread body, and a distal end, on the opposite side of the base.
 "Distal end": relates herein to one of the two longitudinal ends of a barb opposite the proximal end in contact with the thread body. The distal end of the barb is the end of the barb intended to fasten the peripheral tissue on the passage of the thread.

"Substantially" followed by a numeric value should be understood as "plus or minus 15%, 10%, 5%, 4%, 3%, 2% or 1%".

BRIEF DESCRIPTION OF THE FIGURES

The features and the advantages of the invention will emerge in the following description of embodiments of a surgical thread and of a method for manufacturing a surgical thread according to the invention, given merely by way of example and with reference to the appended drawings wherein.

DETAILED DESCRIPTION

The present invention relates to a surgical thread for medicine, cosmetic surgery and/or cosmetic medicine comprising at least one portion extending longitudinally, said portion comprising barbs configured to fasten to the subcutaneous and superficial muscle tissue.

Figure 1:
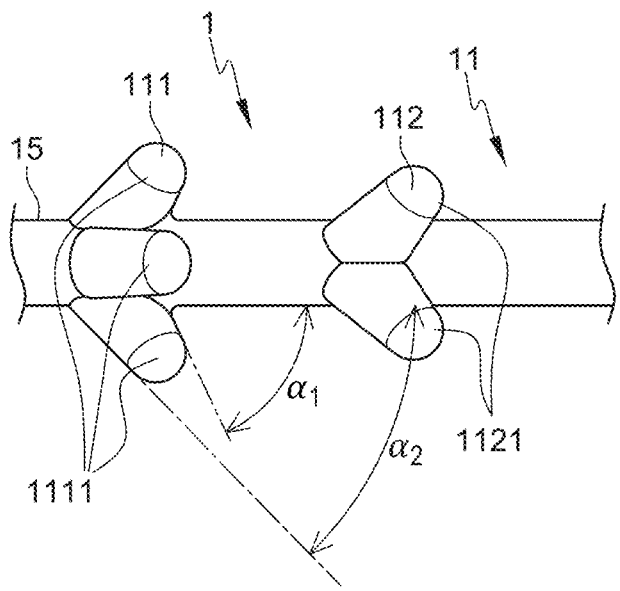
FIG. 1 is a side view of the first portion of the surgical thread according to an embodiment of the present invention.

The surgical thread 1 illustrated in FIG. 1 extends longitudinally and comprises at least one portion comprising fastening means 111, 112. These fastening means 111, 112 are arranged longitudinally along the portion of the surgical thread 1.

The surgical thread 1 comprises a central thread 14 covered with a sheath 15. The central thread 14 may be made of polyamide (monofilament or multifilament), polyethylene, or polypropylene. Preferentially, the central thread is made of polyester or polyethylene terephthalate. According to an advantageous embodiment, the central thread 14 comprises braided filament yarns, particularly polyester or polyethylene terephthalate filament yarns. The sheath 15 may be made of plastic material, preferentially of plastic material having a small elongation variation as a function of a temperature or tension variation sustained by the surgical thread 1 such as polyurethane elastomer or silicone.

The sheath 15 comprises fastening means 111, 112. The fastening means 111, 112 are formed with the sheath 15, without cutting, directly in the form of conical or substantially conical barbs each having an angle of inclination between 10° and 75° with the longitudinal axis of the surgical thread. In an embodiment, the fastening means 111, 112 are obtained by moulding the sheath 15. In an embodiment, the fastening means 111, 112 are not obtained by cutting, in the longitudinal direction of the thread, a thin part of the thread body. According to an embodiment, the surgical thread 1 is obtained by placing the central thread 14 in a mould, the material of the sheath 15 being injected into the mould around the central thread 14.

The surgical thread 1 therefore comprises a thread body (or core) and fastening means 111, 112. The thread body is formed by the central thread 14 and the part of the sheath 15 comprising no fastening means 111, 112.

In an embodiment, the surgical thread body has a thickness or a diameter which varies from 0.25 to 0.75 mm, preferentially from 0.40 to 0.60 mm, and very preferentially from 0.45 to 0.55 mm. In an embodiment, the thickness of the thread body is substantially equal to 0.25 mm, 0.30 mm, 0.35 mm, 0.40 mm, 0.45 mm, 0.50 mm, 0.55 mm, 0.60 mm, 0.65 mm, 0.70 mm or 0.75 mm.

As illustrated in FIG. 1, the fastening means comprises conical or substantially conical barbs 1111 and 1121.

In an embodiment, the surgical thread 1 extends longitudinally and comprises a central thread 14 and a sheath 15; said sheath 15 comprises at least a first portion 11 and comprises fastening means 111, 112 each comprising at least one conical barb 1111, 1121.

In an embodiment, the barbs do not have a cylindrical shape.

The term conical barbs denotes a volume defining a base of the barb, a distal end of the barb and a longitudinal axis of the barb passing through the centre of the base of the barb and through the centre of the distal end of the barb. Finally, the cross-section of the barb along an orthogonal axis to the longitudinal axis of the barb is strictly tapering from the base to the distal end. In an embodiment, the conical barbs have more specifically a truncated shape.

In an embodiment, the barbs have a height which varies from 0.30 to 1 mm, preferentially from 0.40 to 0.50 mm. In an embodiment, the barbs have a height substantially equal to 0.35 mm, 0.40 mm, 0.45 mm, 0.50 mm, 0.55 mm, 0.60 mm, 0.65 mm, 0.70 mm, 0.75 mm, 0.80 mm, 0.85 mm, 0.90 mm, 0.95 mm or 1 mm.

The term height denotes the distance between the distal end of a barb and the thread body.

In the embodiment shown in the figures, the conical barb has straight edges. Alternatively, the shape of the barb may also be a combination between a conical shape and a curved shape. In this case, the longitudinal axis of the barb has a radius of curvature.

In an embodiment, the longitudinal axis of the barb is not merged with the longitudinal axis of the surgical thread 1 and the longitudinal axis of the barb has an angle of inclination with the longitudinal axis of the surgical thread 1.

In an embodiment, the angle of inclination is not equal to 90° or is not equal to 0°.

In an embodiment, the angle of inclination is greater than 10°. In an embodiment, the angle of inclination varies from 30 to 75°, from 35° to 70°, from 40° to 65°, from 45° to 60° or from 50 to 55°. The angle of inclination is the median axis of the angles $\alpha_1$ and $\alpha_2$ illustrated in FIG. 1.

In a plane comprising at least one barb and the longitudinal axis of the thread body as illustrated in FIG. 1, the two opposing axes on the surface of the barb form angles $\alpha_1$ and $\alpha_2$ with the longitudinal axis of the central thread 14 or thread body. To form barbs of substantially conical shape, the angles ($\alpha_1$ and $\alpha_2$) formed by these two edges and the longitudinal axis of the thread body are different such that the cross-section of the barb tapers from the base of the barb to the distal end thereof.

In an embodiment, the angle $\alpha_1$ is greater than the angle $\alpha_2$.

In an embodiment, the difference between these two angles ($\alpha_1$ and $\alpha_2$) varies from 30° to 5°, from 25° to 8° or from 20° to 10°. The term "difference" between two angles denotes the absolute subtraction value between the two angles.

In an embodiment, $\alpha_1$ varies from 80° to 30°, from 75° to 35°, from 75° to 45°, from 70° to 50°, from 65° to 55°, from 75° to 70°, from 70° to 65°, from 65° to 60°, from 60° to 55°, from 55° to 50°, or from 62° to 58°. In an embodiment, $\alpha_2$ varies from 70° to 10°, from 65° to 15°, from 60° to 20°, from 55° to 30°, from 50° to 40°, from 30° to 35°, from 35° to 40°, from 45° to 50°, from 50° to 55°, from 55° to 60° or from 47° to 43°.

Figure 3:
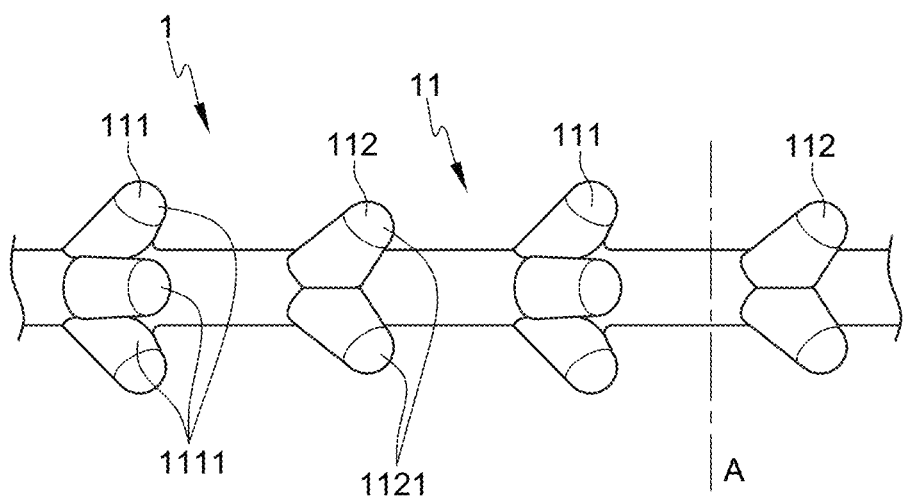
FIG. 3 is a side view of the first portion of the surgical thread according to an embodiment where the barbs have a conical shape and a rounded distal end.

In an embodiment illustrated in FIG. 3, where the surgical thread 1 comprises a plurality of barbs on a portion, the barbs of the surgical thread 1 of the same portion are inclined such that the distal ends of the barbs "point" towards the same longitudinal end of the surgical thread 1. In other words, the base of the barb is farther from this end of the thread than the distal end of the barb when the surgical thread 1 is taut.

The angle of inclination makes it possible to reinforce the fastening of the fastening means in the subcutaneous and superficial muscle tissue, by minimising the risk of tearing and turning of the barb in the case of significant tensioning of the device. This effect is increased when the barbs are of a shape favouring penetration in the subcutaneous and superficial muscle tissue, as described above.

In an embodiment, the distal end of the fastening means has a blunted shape. Preferably, the distal end of the barbs of the fastening means has a spherical or rounded or substantially spherical or rounded shape. In an embodiment, the distal end of the barbs of the fastening means has a radius of curvature which varies from 0.10 to 0.25 mm, from 0.15 to 0.21 mm, from 0.10 to 0.15 mm, from 0.15 to 0.20 mm, from 0.20 to 0.25 mm or preferentially from 0.175 to 0.185 mm.

This spherical or rounded shape of the distal end of the barbs facilitates the removal of the threads from the face, causing no sequelae or permanent marks on the patient's face.

In an embodiment, the distal end is not situated on the longitudinal axis of the surgical thread 1.

According to the invention, each fastening means comprises at least one conical barb.

Figure 2A:
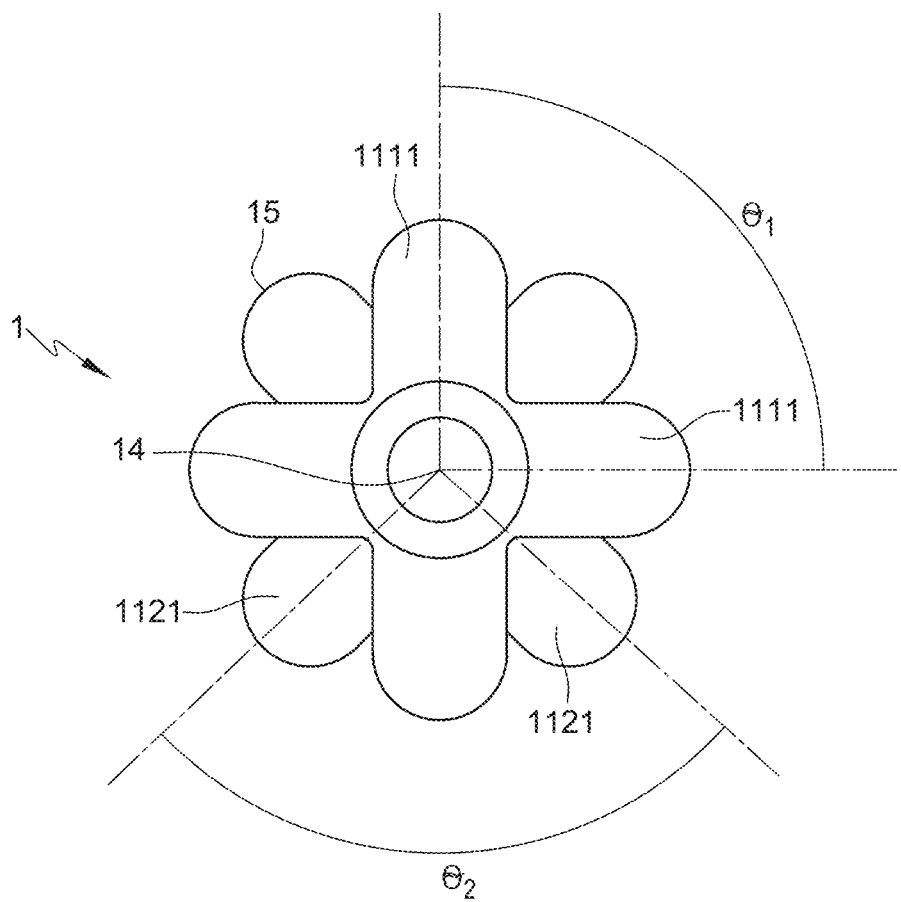
FIGS. 2A, and 2B are cross-sectional views along the axis A of FIG. 3 of the first portion of the surgical thread according to an embodiment of the present invention.

In an embodiment, the fastening means comprise N barbs 1111 not spaced longitudinally (as illustrated in FIG. 3) and regularly spaced angularly by an angle $\theta_1$ (as illustrated in FIG. 2A). Thus, the fastening means consist of N barbs, each situated on the same longitudinal level but at different angular levels of the thread. In an embodiment, the angle $\theta_1$ (also referenced $\theta_2$) is different from 0° and from 360°. In an embodiment, the angle $\theta_1$ is equal to 360°/N. N being an integer equal to or greater than 2.

In an embodiment, the fastening means 111 each comprise the same number of barbs 1111, 1121. Indeed, during the use of the surgical thread, the tension applied along the thread is better distributed in the longitudinal direction when the fastening means 111 and 112 all comprise the same number of barbs 1111 and 1121.

In an embodiment, the fastening means 111 comprise 2 barbs, 3 barbs, 4 barbs, 5 barbs, 6 barbs, 7 barbs, 8 barbs or at least 9 barbs.

In an embodiment, each fastening means 111 is spaced longitudinally from the adjacent fastening means 112 thereof by a pitch p. Thus, the first portion 11 comprises a regular longitudinal series of fastening means 111, 112.

By a longitudinal spacing by a pitch p, it is necessary to understand herein a longitudinal spacing by a pitch p at plus or minus 15%, preferentially at plus or minus 10%, very preferentially at plus or minus 5%.

The pitch p may vary from 0.25 mm to 10 mm. In a preferential embodiment, the pitch p may vary from 1 mm to 2 mm. Very preferentially, the pitch p may vary from 1.25 mm to 1.75 mm. In an embodiment, the pitch p is substantially equal to 0.25 mm, 0.5 mm, 1 mm, 1.5 mm, 2 mm, 2.5 mm, 3 mm, 3.5 mm, 4 mm, 5 mm, 6 mm, 7 mm, 8 mm, 9 mm or 10 mm.

In an embodiment, all the fastening means situated on the same portion comprise the same number of barbs N.

In an embodiment illustrated in FIG. 3, all the fastening means situated on the same portion comprise the same number of barbs N and each fastening means 111 is offset angularly with respect to the adjacent fastening means 112 thereof.

Figure 2B:
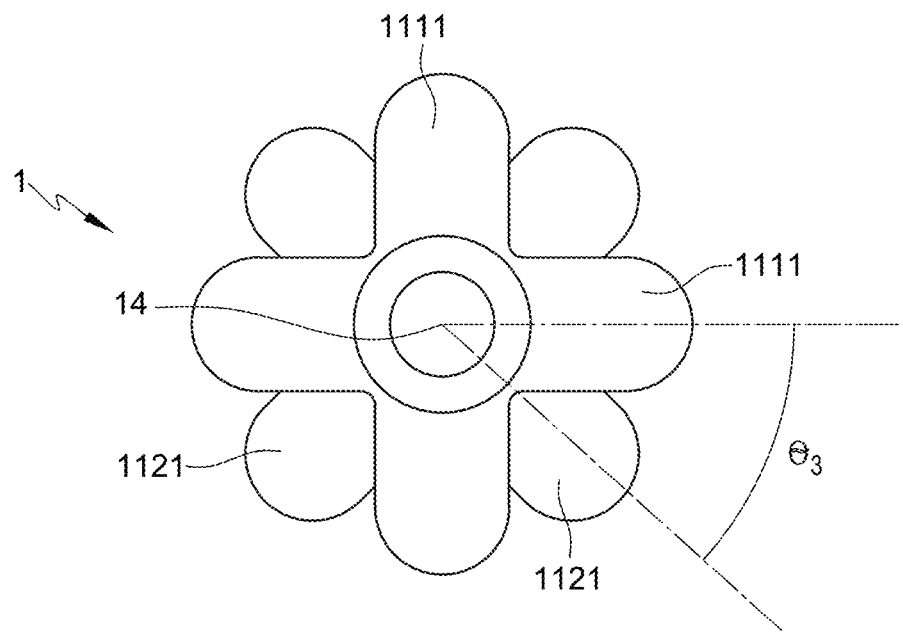

As shown in FIG. 2B, each fastening means 111 is offset in rotation by an angle $\theta_3$ with respect to the adjacent fastening means 112 thereof. In an embodiment, the angle $\theta_3$ is strictly greater than 0° and strictly less than the angle $\theta_1$. In an embodiment, the angle $\theta_3$ is different from 0° and from 360° or is different from a multiple of 360°/N. In an embodiment, the angle $\theta_3$ is greater than 5°, 10° or 15°. In a preferential embodiment, the angle $\theta_3$ is equal to 360°/($x$ N) where x is a positive integer equal to or greater than 2. Very preferentially, the angle $\theta_3$ is substantially equal to 360°/(2N) or 360°/(3N).

In this embodiment, the angle of rotation between each adjacent fastening means is the same. The stress is thus distributed substantially equally on several regular axes. This makes it possible to distribute the stress applied by the barbs of the thread on the subcutaneous and superficial muscle tissue as homogeneously as possible and makes it possible to optimise the effectiveness of the fastening of the thread to the subcutaneous and superficial muscle tissue.

Thus, the portion of the surgical thread is composed, longitudinally, of a plurality of fastening means wherein the barbs are offset angularly with the barbs of the subsequent and preceding fastening means.

In the embodiment where the angle $\theta_3$ is substantially equal to 360°/(2N), the portion of the surgical thread is composed, longitudinally, of a plurality of first fastening means and second fastening means, in alternation.

This alternation of first fastening means and second fastening means, offset longitudinal and angularly enables superior fastening of said surgical thread 1 in the subcutaneous and superficial muscle tissue and a superior tensile strength of the thread in the subcutaneous and superficial muscle tissue.

In a preferential embodiment, the fastening means 111 and 112 each comprise 4 conical barbs, the angles $\theta_1$ are substantially equal to 90° and $\theta_3$ is substantially equal to 45°.

In this embodiment, the portion of the surgical thread comprises first and second fastening means 111, 112 arranged longitudinally in alternation along the first portion of the surgical thread, and the barbs of the first fastening means 1111 are offset angularly by an angle of 45° with the barbs of the second fastening means 1121.

Figure 4:
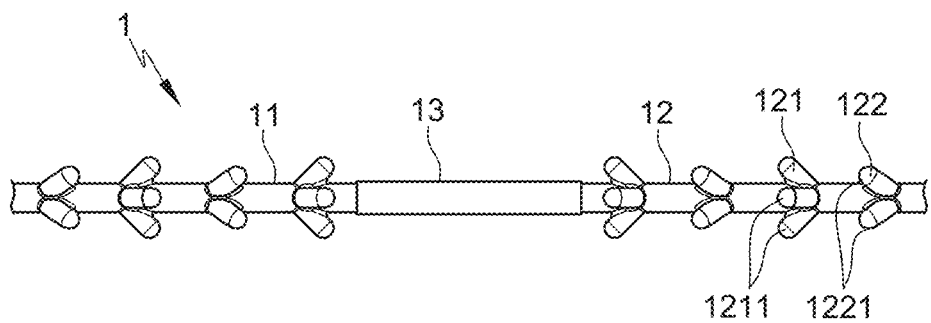
FIG. 4 is a schematic side view of the surgical thread according to an embodiment of the present invention comprising two portions including fastening means and a central portion devoid of fastening means.

In an embodiment illustrated in FIG. 4, the surgical thread 1 comprises a first portion 11 according to the present invention and a second portion 12, similar to the first portion 11, as well as a third portion 13 devoid of fastening means. The third portion 13 is situated between the first portion 11 and the second portion 12.

Similarly to the first portion 11, the second portion 12 comprises fastening means 121, 122 and conical barbs 1211, 1221 the embodiments whereof are the same as those of the first portion 11.

This series of two portions comprising fastening means and a central portion 13 comprising none makes it possible to enhance the precision of the fastening of the subcutaneous and superficial muscle tissue. In this embodiment, the surgical thread 1 passes twice under the skin, on either side of the central third portion.

In an embodiment, at least one portion of the central third portion 13 is coloured. It may be coloured with a different colour from the colour of the first portion 11 and the second portion 12. In an embodiment, the central third portion 13 is coloured with an injected ink, preferentially a black ink. Colouring this central portion 13 enables the surgeon to view this portion easily. In an alternative embodiment, the central third portion 13 is coloured by adding a black silicone sheath. Thus, the surgeon will insert the surgical thread 1 under the patient's skin such that the entirety of the first portion and the second portion 11, 12 is inserted. Finally, the surgeon will be able to insert the central portion 13.

In an embodiment, the barbs of the fastening means of the first 11 and the second portion 12 are inclined with respect to the longitudinal axis of the thread 1 in the direction of the third portion 13.

The term "inclined in the direction of the third portion 13" denotes herein that the base of the barbs in contact with the longitudinal axis of the surgical thread 1 is farther from the central third portion 13 than the distal end of the corresponding barb.

In an embodiment, the first portion 11 is symmetrical with the second portion 12 along an axis passing through the mid-point of the central third portion 13. In an embodiment, the central thread 14 is covered with two sheaths 15 according to the present invention forming the first 11 and the second portion 12.

Figure 6:
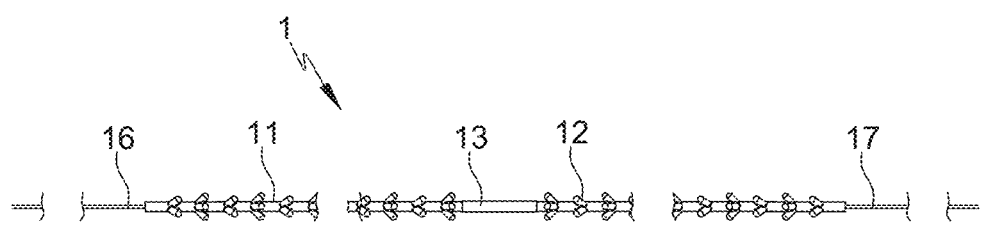
FIG. 6 is a side view of the surgical thread according to an embodiment of the present invention comprising two extension portions at the ends thereof.

In an embodiment illustrated in FIG. 6, the central thread 14 extends from the first portion 11 and the second portion 12 in the opposite direction to the third portion 13. These extensions 16, 17 are completely devoid of sheath or fastening means. In this way, the surgeon can handle both ends of the thread easily.

In an embodiment, these extensions 16, 17 of the surgical thread 1 make it possible to attach the surgical thread 1 to a needle by crimping or by inserting the end of the thread into the eye of a surgical needle.

In this embodiment, the surgical thread thus comprises 5 portions:
- two extension portions 16 and 17 at the ends of the surgical thread 1 devoid of fastening means;
- the central third portion 13 devoid of fastening means; and
- the first portion 11 and the second portion 12 each comprising a sheath comprising fastening means and both situated between the central third portion and an extension portion.

In an embodiment, the central third portion 13 has a length which varies from 2 mm to 30 mm, 3 mm to 10 mm, from 4 mm to 6 mm, or substantially equal to 5 mm. in a further embodiment, the central third portion 13 has a length which varies from 15 mm to 25 mm, from 18 mm to 23 mm or substantially equal to 20 mm.

The length of the first 11 and/or the second portion 12 varies according to the location on the face or body where the thread according to the invention will be used. In an embodiment, the first portion 11 and/or the second portion 12 have a length which varies from 50 to 300 mm, or from 60 to 200 mm. In an embodiment, the length of the first 11 and/or the second portion 12 is substantially equal to 50, 60, 70, 80, 90, 100, 110, 120, 130, 140, 150, 160, 170, 180, 190, 200, 225, or 250 mm.

In a first preferential embodiment, the surgical thread comprises a first portion 11 and a second portion 12 wherein the length varies from 80 mm to 100 mm or from 85 mm to 95 mm and a central third portion 13 wherein the length varies from 15 mm to 25 mm or from 18 to 22 mm. In a second preferential embodiment, the surgical thread 1 comprises a first portion 11 and a second portion 12 wherein the length varies from 160 mm to 135 mm or from 150 mm to 145 mm and a central third portion 13 wherein the length varies from 3 mm to 10 mm or from 4 to 6 mm.

In an embodiment, the extension portions 16, 17 at the ends of the surgical thread 1 devoid of fastening means have a length which varies from 170 mm to 120 mm or from 165 mm to 155 mm. In a further embodiment, the extension portions 16, 17 at the ends of the surgical thread 1 devoid of fastening means have a length which varies from 160 mm to 240 mm or from 190 mm to 210 mm. In a further embodiment, the extension portions 16, 17 at the ends of the surgical thread 1 devoid of fastening means have a length which varies from 200 mm to 300 mm or from 230 mm to 270 mm. In an embodiment, the thickness or the diameter of the extension portions 16, 17 varies from 0.10 mm to 0.35 mm, or from 0.15 to 0.25 mm, preferentially from 0.20 to 0.25 mm.

In an embodiment, the method for manufacturing the surgical thread 1 comprises the formation of the fastening means during the manufacture of the or each sheath 15 fitted on the thread, directly in the form of conical barbs each having an angle of inclination between 10° and 75° with the longitudinal axis of the surgical thread 1.

In an embodiment, the surgical thread 1 is obtained by placing the central thread 14 in a mould and by injecting the material of the sheath 15 into the mould around the central thread.

The invention also relates to a medical device comprising a surgical thread 1 according to the present invention also comprising a surgical needle at one end of the surgical thread 1 or at an extension portion 16 or 17.

In an embodiment, the medical device comprises two surgical needles, each being attached to an end of the surgical thread 1 or each being attached to an extension portion 16, 17.

In an embodiment, the needle is attached to the surgical thread 1 by crimping.

In a further embodiment, the needle comprises an eye and is attached to the surgical thread 1 by inserting said thread 1 into the eye of the needle.

EXAMPLES

Materials and Methods

Materials

Figure 5:
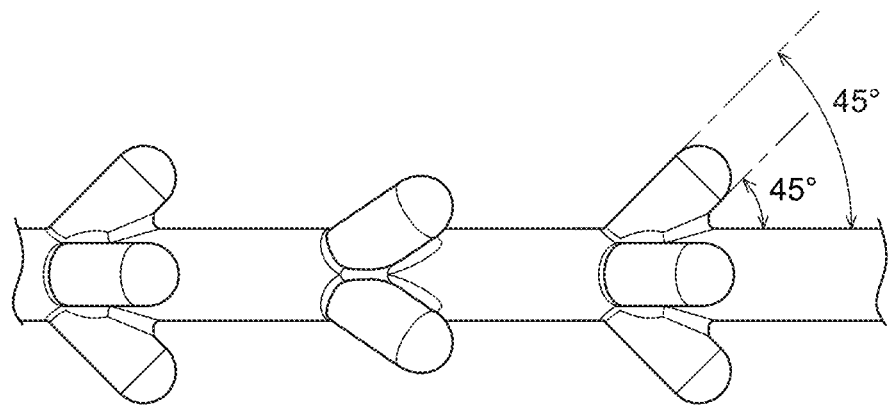
FIG. 5 is a side view of a thread comprising cylindrical barbs.

Two types of surgical threads are used: the first type of thread (illustrated in FIG. 3) comprises conical barbs and the second type of thread comprises cylindrical barbs (illustrated in FIG. 5).

Methods

The purpose of these tests is to compare the maximum strength value of each type of thread through animal tissue. The thread is inserted into an animal muscle tissue sample using a needle. The muscle tissue sample is then fixed to the movable part of a traction bench using a holding support.

The end of the thread is fixed to a self-closing grappler so as to pull in the opposite direction of the barbs. The speed of the traction bench is set to 30 mm/min. The maximum force measured after the thread has passed completely through the animal tissue is noted.

The tests were carried out on pork fillet in order to obtain the most homogeneous insertion medium possible and in order to remove the risks of having the presence of a nerve or a different muscular density liable to disrupt the comparative tests. So that the results are not temperature-dependent, the animal tissue samples are placed at ambient temperature 30 min before the tests.

Results

Out of a total of 20 samples of a length of 45 mm of each thread type, the mean maximum force measured with the threads comprising conical barbs is 4.80 N whereas that for the threads comprising cylindrical barbs is 3.98 N (see table below).

|  | Conical barb thread | Cylindrical barb thread |
|---|---|---|
|  | Force measured (N) |  |
| Sample 1 | 3.06 | 2.64 |
| Sample 2 | 4.68 | 3.86 |
| Sample 3 | 4.94 | 3.44 |
| Sample 4 | 4.28 | 2.18 |
| Sample 5 | 5.18 | 3.38 |
| Sample 6 | 3.94 | 4.02 |
| Sample 7 | 4.48 | 3.06 |
| Sample 8 | 4.10 | 4.06 |
| Sample 9 | 5.98 | 4.06 |
| Sample 10 | 3.10 | 4.28 |
| Sample 11 | 5.44 | 4.70 |
| Sample 12 | 6.04 | 4.88 |
| Sample 13 | 5.70 | 5.72 |
| Sample 14 | 4.58 | 4.16 |
| Sample 15 | 5.86 | 2.78 |
| Sample 16 | 4.72 | 3.98 |
| Sample 17 | 5.22 | 4.46 |
| Sample 18 | 5.10 | 5.46 |
| Sample 19 | 4.30 | 3.80 |
| Sample 20 | 5.28 | 4.70 |
| MEAN (N) | 4.80 | 3.98 |

The maximum force of a thread comprising conical barbs is therefore more than 20% greater than that of a thread comprising cylindrical barbs. The conical shape of the thread barbs therefore enables superior fastening in the tissue than a cylindrical shape.

REFERENCES

1—Surgical thread;
11—First portion;
111, 112—Fastening means of the first portion;
1111, 1121—Conical barbs of the first portion;
12—Second portion;
121, 122—Fastening means of the second portion;
1211, 1221—Conical barbs of the second portion;
13—Third portion;
14—Central thread;
15—Sheath;
16—First extension portion;
17—Second extension portion.

The invention claimed is:

1. A surgical thread comprising:
at least a first portion extending longitudinally and comprising a central thread covered with a sheath, said sheath comprising a plurality of series of conical barbs, each series of conical barbs comprising at least one conical barb, wherein the at least one conical barb of each series of conical barbs is offset in rotation by an angle $\theta_3$ with respect to the at least one conical barb of an adjacent series of conical barbs, wherein the angle $\theta_3$ is different from 0° and from 360°;
wherein each series of conical barbs comprises N conical barbs not spaced longitudinally and regularly spaced angularly by an angle $\theta_1$ and wherein N is an integer equal to or greater than 2; and
wherein the angle $\theta_3$ is strictly less than the angle $\theta_1$.

2. The surgical thread according to claim 1, wherein the angle $\theta_3$ is substantially equal to 45°.

3. The surgical thread according to claim 1, wherein the plurality of series of conical barbs is formed with the sheath in the form of conical barbs each having an angle of inclination between 10° and 75° with the longitudinal axis of the surgical thread.

4. The surgical thread according to claim 1, further comprising:
a second portion extending longitudinally and comprising the central thread covered with the sheath comprising a plurality of second series of conical barbs each second series of conical barbs comprising at least one conical barb; and
a third portion devoid of conical barbs and situated between the first portion and the second portion.

5. The surgical thread according to claim 4, wherein the at least one conical barb of the first portion and the at least one conical barb of the second portion are inclined with respect to the longitudinal axis of the surgical thread in the direction of the third portion.

6. The surgical thread according to claim 1, wherein the conical barbs are inclined and form an angle with respect to the longitudinal axis of the surgical thread of substantially 60°.

7. The surgical thread according to claim 1, wherein said conical barbs comprise a spherical or rounded distal end.

8. The surgical thread according to claim 1, wherein each series of conical barbs comprises the same number N of conical barbs.

9. The surgical thread according to claim 1, wherein each series of conical barbs comprises four conical barbs.

10. The surgical thread according to claim 1, wherein the central thread comprises a textile material including filament yarns, particularly braided or woven filament yarns.

11. The surgical thread according to claim 1, wherein the central thread is made of polyester and/or the sheath is made of silicone or polyurethane elastomer.

12. The surgical thread according to claim 1, wherein the conical barbs are obtained by moulding the sheath.

13. The surgical thread according to claim 1, further comprising an extension portion at each longitudinal end of the surgical thread.

* * * * *